US008426393B2

(12) United States Patent
Fox et al.

(10) Patent No.: US 8,426,393 B2
(45) Date of Patent: Apr. 23, 2013

(54) INHALED COMBINATION THERAPY

(75) Inventors: Justian Craig Fox, Harlow (GB); Mary Frances Fitzgerald, Harlow (GB); Harry Finch, Harlow (GB)

(73) Assignee: Pulmagen Therapeutics (Synergy) Limited, Burnham (GB)

( * ) Notice: Subject to any disclaimer, the term of this patent is extended or adjusted under 35 U.S.C. 154(b) by 0 days.

(21) Appl. No.: 12/862,421

(22) Filed: Aug. 24, 2010

(65) Prior Publication Data

US 2010/0324002 A1 Dec. 23, 2010

Related U.S. Application Data

(62) Division of application No. 11/883,635, filed as application No. PCT/GB2006/000482 on Feb. 13, 2006.

(30) Foreign Application Priority Data

Feb. 11, 2005 (GB) .................................. 0502949.1
Dec. 22, 2005 (GB) .................................. 0526124.3

(51) Int. Cl.
*A01N 45/00* (2006.01)
*A61K 31/56* (2006.01)

(52) U.S. Cl.
USPC ........................................................ 514/171

(58) Field of Classification Search .................... 514/171
See application file for complete search history.

(56) References Cited

U.S. PATENT DOCUMENTS

| 5,736,124 A * | 4/1998 | Akehurst et al. ................. 424/45 |
| 6,025,360 A | 2/2000 | Miller |
| 2003/0134865 A1 | 7/2003 | Adcock |
| 2004/0105819 A1 | 6/2004 | Hale et al. |
| 2005/0026848 A1 | 2/2005 | Robinson |
| 2005/0089478 A1* | 4/2005 | Govind et al. .................. 424/46 |

FOREIGN PATENT DOCUMENTS

| EP | 0421587 | | 4/1991 |
| EP | 1080720 | | 3/2001 |
| EP | 1 080 720 | * | 7/2001 |
| FR | 3622 M | | 10/1965 |
| WO | 93/15741 | | 8/1993 |
| WO | 2005/011608 | | 2/2005 |
| WO | WO 2005/011594 A2 | | 2/2005 |
| WO | WO 2005/011595 A2 | | 2/2005 |
| WO | WO 2005/011602 A2 | | 2/2005 |
| WO | WO 2005/011604 A2 | | 2/2005 |
| WO | WO2005/011608 | * | 2/2005 |
| WO | WO 2005/011608 A2 | | 2/2005 |
| WO | WO 2005/011613 A2 | | 2/2005 |
| WO | WO 2005/011615 A2 | | 2/2005 |
| WO | 2006/013359 | | 2/2006 |

OTHER PUBLICATIONS

Weiner et. al. (Chest (1995) 108:1568-1571).*
Barnes (American Journal of Respiratory and critical care medicine (2003) 167: 813-818).*
Markham et. al. (Drugs (1998) 56:1081-1091).*
Giembycz, "Cilomilast: a second generation phosphodiesterase 4 inhibitor for asthma and chronic obstructive pulmonary disease." Exper Opinion on Investigational Drugs 10: 1361-1379, 2001.
Barnes et al. "theophylline in the management of asthma: time for reappraisal?" Eur. Respir. J. 7:579-591, 1994.
Markham et al. "Theophylline: A review of its potential steroid sparing effects in asthma" Drugs 56:1081-1091, 1998.
Fontana et al. "Effect of aminophylline aerosol on the bronchial response . . . " Respiration 54:241-246, 1988.
Thompson et al. "The use of aminophylline by inhalation." Br. J. Clin. Pharmacol. 14:463-464, 1982.
Cushley et al. "Bronchodilator actions of xanthine derivatives administered by onhalation in asthma" thorax 40:176-179, 1985.
Cosio et al. "Theophylline restores histone deacetylase activity and steroid responses in COPD macrophages" J. Exp. Med. 200:689-695, 2004.
Barnes "Theophylline, New pperspectives for an old drug" Am. J. Respir. Crit. Care Med. 167:813-818, 2003.
Ouagued "The novel phosphodiesterase 4 inhibitor, CI-1044, inhibits LPS-induced TNF-alpha production in whole blood from COPD patients" Pulm. Pharmacol. Ther. 18:49-54, 2004.
Bel "Severe asthma" Breathe 3:128-139, 2006.
Napp Pharmaceuticals Ltd. "Uniphyllin continus tablets, summary of product characteristics . . . " Print out of http://emc.medicines.org.uk/medicine/1233/SPC/Uniphyllin+Continus+tablets/ , last visited Apr. 28, 2009.
Lim et al. "Comparison of high dose inhaled steroids, low dose inhaled steroids plus low dose theophylline, and low dose inhaled steroids alone in chronic asthma in general practice." Thorax 55:837-841, 2000.
Evans et al. (1997) A comparison of low-dose inhaled budesonide plus theophylline and high-dose inhaled budesonide for moderate asthma, N. Engl. J. Med. 337:1412-1418.
Lim et al. (1998) A randomised, double blind placebo-controlled comparison of low dose theophylline plus low dose inhaled steroids vs. high dose inhaled steroids in the management of asthma, Am. J. Respir. Crit. Care Med. 157:A415.
Morali et al. (2001) Efficacy of Inhaled Budesonide and Oral Theophylline in Asthmatic Subjects, J. Asthma 38:673-679.
Rivington et al. (1995) Efficacy of Uniphyl, Salbutamol, and Their Combination in Asthmatic Patients on High-dose inhaled steroids, Am. J. Respir. Crit. Care Med. 151:325-32.
Suessmuth et al. (2003) Low-dose theophylline in childhood asthma: a placebo-controlled, double-blind study, Pediatr. Allergy Immunol. 14:394-400.
Ukena et al. (1997) Comparison of addition of theophylline to inhaled steroid with doubling dose of inhaled steroid in asthma, Eur. Respir. J. 10:2754-2760.
Wrenn et al. (1991) Aminophylline Therapy for Acute Bronchospastic Disease in the Emergency Room, Annals Intern. Med. 115:241-247.
Eyles et al., "Immunological responses to nasal delivery of free and encapsulated tetanus toxoid: studies on the effect of vehicle volume", Int. J. Pharm., 189(1): 75-79 (1999). (Abstract).

(Continued)

*Primary Examiner* — Marcos Sznaidman
(74) *Attorney, Agent, or Firm* — Morgan, Lewis & Bockius LLP (57) ABSTRACT

There is provided the use of a methylxanthine derivative such as theophylline and a steroid in a synergistic combination for the treatment of chronic obstructive pulmonary disease, wherein the combination is administered by the inhaled route for pulmonary delivery.

13 Claims, 5 Drawing Sheets

OTHER PUBLICATIONS

Geelhaar et al., "Morphometric estimation of pulmonary diffusion capacity. 3. The effect of increased oxygen consumption in Japanese Waltzing mice", Respir. Physiol., 11(3): 354-366 (1971).

Guidance for Industry: Estimating the Maximum Safe Starting Dose in Intial Clinical Trials for Therapeutics in Adult Healthy Volunteers, U.S. Food and Drug Administration (FDA) (2005), http://www.fda.gov/Cder/Guidance/5541fnl.pdf.

Karrer, "The ultrastructure of mouse lung: the alveolar macrophage", J Biophys. Biochem. Cytol., 4(6): 693-700 (1958).

Shen, et al., "The effects of intranasal budesonide on allergen-induced production of interleukin-5 and eotaxin, airways, blood, and bone marrow eosinophilia, and eosinophil progenitor expansion in sensitized mice", Am. J. Respir. Crit. Care Med., 166(2): 146-153 (2002).

Kokubu (1995) Bronchodilating effect of inhalation of aeroslized aminphylline in asthmatic patients, Allergy, 44:1379-1386.

Yeager et al. (1995) Protective effects of inhaled aminophylline on methacoline-induced airway responses in greyhound dogs, Current Therapeutic Research, 56:47-56.

Stewart et al. (1976) A trial of Aerosolized Theophyline in Relieving Brochospasm, Chest, 69:718-721.

Dal Negro et al. (2004 Salmeterol & fluticasone 50 microg/250 microg bid in combination provides a better long-term control than salmeterol 50 microg bid alone and placebo in COPD patients already treated with theophylline, Pulm. Pharmacol. Ther., 16:241-246.

Cazzola et al. (2004) Salmeterol/fluticasone propionate in a single inhaler device versus theophylline + fluticasone propionate in patients with COPD, Pulm. Pharmacol. Ther., 17:141-145.

Bone et al. (1994) In chronic pulmonary disease, a combination of ipratropium and albuterol is more effective than either agent alone, Chest, 105:1411-1419.

Bohadana et al. (1980) The bronchodilator action of theophylline earosol in subjects with chronic airflow obstruction Bull. Eur. Physiopathol Respir., 16:13-24.

Cushley et al. (1985) Bronchodilator actions of xanthine derivatives administered by inhalation in asthma, Thorax 40: 176-179.

\* cited by examiner

INHALED COMBINATION THERAPY

CROSS-REFERENCE TO RELATED APPLICATIONS

The present application is a divisional of U.S. patent application Ser. No. 11/883,635 (filed Apr. 4, 2008), which is a U.S. National Phase Application of International Application PCT/GB2006/000482 (filed Feb. 13, 2006), which claims the benefit of GB 0502949.1 (filed Feb. 11, 2005) and GB 0526124.3 (filed Dec. 22, 2005) all of which are hereby incorporated by reference in their entirety.

The present invention provides the inhaled use of methylxanthine derivatives such as theophylline and steroid drugs in a synergistic combination for manufacture of a medicament in the treatment of chronic respiratory diseases such as chronic obstructive pulmonary disease (COPD). The administration of a methylxanthine and a steroid in combination administered via the inhaled route for pulmonary delivery, results in a therapeutic synergistic pulmonary anti-inflammatory response.

INTRODUCTION

Theophylline is an inexpensive white crystalline powder used as an oral agent for chronic respiratory diseases such as asthma and COPD. Aminophylline, or theophylline ethylenediamine, is a combination of theophylline and ethylenediamine and has similar properties. Theophylline is known to have a bronchodilating effect and a mild anti-inflammatory effect, due in part to its activity as a weak nonselective phosphodiesterase (PDE) inhibitor. The drug has hitherto been characterised by a narrow therapeutic index, and toxicity to this agent, marked by gastrointestinal upset, tremor, cardiac arrhythmias, and other complications, is common in clinical practice. Other drugs for chronic respiratory diseases, such as inhaled beta-agonists, inhaled anti-cholinergics and inhaled steroids, are often prescribed instead of oral theophylline to avoid its adverse effects. However, to date there has been limited investigation of the therapeutic potential of inhaled theophylline in the treatment of chronic respiratory diseases such as COPD and asthma.

Although theophylline has been in clinical use for many years, its molecular mechanism of action and its site of action remain uncertain. Several molecular mechanisms of action have been proposed, including the following.

Theophylline is a weak and nonselective inhibitor of phosphodiesterases, which break down cyclic nucleotides in the cell, thereby leading to an increase in intracellular cyclic AMP and GMP concentrations. Theophylline relaxes airway smooth muscle by inhibition of PDE activity (PDE3, PDE4 and PDE5), but relatively high concentrations are needed for maximal relaxation (Rabe, et al. Eur Respir J 1999, 8: 637-42). The degree of PDE inhibition is very small at concentrations of theophylline that are therapeutically relevant. There is no evidence that theophylline has any selectivity for any particular isoenzyme, such as, for example, PDE4B, the predominant PDE isoenzyme in inflammatory cells that mediates anti-inflammatory effects in the airways.

Theophylline increases interleukin-10 release, which has a broad spectrum of anti-inflammatory effects. This effect may be mediated via PDE inhibition, although this has not been seen at the doses that are effective in asthma (Oliver, et al. Allergy 2001, 56: 1087-90).

Theophylline prevents the translocation of the proinflammatory transcription factor nuclear factor-κB (NF-κB) into the nucleus, thus potentially reducing the expression of inflammatory genes in asthma and COPD (Tomita, et al. Arch Pharmacol 1999, 359:249-55). These effects are seen at high concentrations and may also be mediated by inhibition of PDE. It is likely therefore, that PDE inhibition is not a mechanism of action of theophylline when administered at low oral doses (<10 mg/L).

Theophylline is also a potent inhibitor of adenosine receptors at therapeutic concentrations, with antagonism of $A_1$ and $A_2$ receptors, although it is less effective against $A_3$ receptors (Pauwels & Joos, Arch Int Pharmacodyn Ther 1995, 329: 151-60). There is a report that inhaled theophylline monotherapy can antagonise the bronchoconstrictor activity of inhaled adenosine in asthmatics (Cushley et al, Am Rev Resp Disease 1984, 129, 380-4). In addition, inhaled theophylline (given as aminophylline) has also been shown to act as bronchodilator in asthmatic patients (Kokubu H. Arerugi. 1995, 44(12):1379-86).

Theophylline has moreover recently been shown to activate histone deacetylase (HDAC). Acetylation of histone proteins is associated with activation of gene function, and it is believed that proinflammatory transcription factors which activate inflammatory genes also cause an increase in histone acetyltransferase activity. By increasing HDAC activity and so deacetylating histone proteins, theophylline is believed to suppress the expression of inflammatory genes (see Barnes P J, J Respir Crit Care Med, 2003, 167:813-818), Theophylline is believed to interact with a key regulatory kinase or phosphatase enzyme in the molecular pathway which results in elevated HDAC activity, although this is yet to be elucidated.

Minimal but significant pulmonary anti-inflammatory activity has been demonstrated by oral theophylline monotherapy in COPD patients using doses of theophylline that gave plasma levels $\leq$10 mg/L but $\geq$5 mg/L (Culpitt et al. Am. J. Respir. Crit. Care Med, 2002, 165(10): 1371-1376, Kobayashi et al, Respirology 2004, 9:249-254).

Glucocorticoid drugs (steroids) have become the therapy of choice in asthma and are widely used in the treatment of COPD, usually in inhaled form. Inhaled steroids are usually administered once or twice daily at a fixed dosage dependent on the properties of the steroid administered. For example, Budesonide is typically administered at doses of 200 mcg, 400 mcg or 800 mcg doses once or twice daily. Fluticasone is typically administered at doses of 50 mcg, 100 mcg, 250 mcg or 500 mcg doses once or twice daily. Ciclesonide is typically administered at doses of 80 mcg, 160 mcg or 320 mcg doses once or twice daily. The absolute pulmonary delivered dose is dependent on many factors (including properties of the steroid used, inhalation device characteristics, inhalant formulation, patient characteristics, and inhalation technique) but is normally significantly less than the total administered.

However, although inhaled steroids are effective in the majority of asthma patients their use in COPD is contentious owing to their lack of demonstrable anti-inflammatory effect in sputum samples (Keatings et al. Am. J. Respir. Crit Care Med, 1997, 155(2):542-8, Culpitt et al. Am. J. Respir. Crit Care Med. 1999, 160, 5(1): 1635-1639, Loppow et al. Respir. Med. 2001, 95(2): 115-121) and their apparent failure to affect disease progression (Burge, et al (2000). BMJ 320: 1297-1303). Other studies examining sputum have suggested that longer treatment periods particularly with high dose inhaled steroids do have measurable but minimal pulmonary anti-inflammatory effects in some patients (Confalonieri et al. Thorax, 1998, 53(7): 583-585, Mirici et al. Clinical Drug Investigation. 2001, 21:835-442, Yildiz et al. Respiration. 2000, 67:71-76).

Assessment of anti-inflammatory activity by examining bronchial biopsies rather than sputum from COPD patients has also been disappointing however. In contrast to that demonstrated in asthma patients, Hattatowa et al. (Am J Respir Crit Care Med. 2002, 165:1592-1596) did not detect significant reductions in the key inflammatory cells in COPD following 3 months treatment with an inhaled steroid (500 mcg Fluticasone administered twice daily). Despite minimal pulmonary anti-inflammatory activity overall, ICS do reduce exacerbation frequency in COPD patients by 20-30%.

It is likely that improving this minimal pulmonary anti-inflammatory activity of inhaled steroids would provide a great benefit to COPD patients resulting in improved health status, improved pulmonary function, improvement in measures of dyspnea and further reduced exacerbation frequency.

Asthma patients who fail to respond to low doses of steroids are administered a higher dose, in the case of budesonide up to 1600 mcg daily. Evans et al., (2004) NEJM 337:1412, suggest that high doses of inhaled steroids may be substituted by administration of a normal glucocorticoid dose, together with a low dose of oral theophylline for use in asthma. Patients were administered 400 mcg of budesonide (the standard dose) together with 250 or 375 mg of theophylline, or 800 mcg of budesonide plus placebo, twice daily. The plasma concentrations of theophylline that were achieved in this study ranged from 2.5 to 17.1 mg/l with a median value of 8.7 mg/l. The effects of these two treatment paradigms were similar suggesting that theophylline has dose sparing effects when given with a steroid. However, at the doses used, patients suffered from drug-related side effects, including gastrointestinal upsets, palpitations, sore throats and other side-effects associated with steroids and/or theophylline therapy. The authors did not determine any effects of the drug combination on inflammation. Similar studies investigating potential dose sparing of inhaled steroids with oral theophylline have not been carried out in COPD patients.

Cazzola et al, (2004) Pulm Pharm Ther 17:141-145, compared the combination of the bronchodilator salmeterol and the steroid fluticasone with the combination of oral theophylline and inhaled fluticasone (500 mcg twice daily) in COPD patients over a period of 4 months. The dose of oral theophylline was titrated to achieve plasma concentrations of 10-20 mg/L as these plasma levels are required for clinical efficacy in terms of bronchodilation. The inflammatory status of these patients was not examined with either therapy.

US20030134865 discloses a screening method for identifying drug-like compound for treating asthma or other inflammatory diseases. It comprises of a xanthine or a related compound to modulate the activity or expression of HDAC. The invention describes the role of steroids in the repression of inflammatory genes. It predicts that theophylline should enhance glucocorticoid actions by enabling glucocorticoids to recruit HDACs with increased activity. Theophylline is used in synergistic effect with the steroids Dexamethasone and Budesonide in enhancing cell HDAC activity and repression of inflammatory genes in vitro.

U.S. Pat. No. 6,025,360 discloses the use of theophylline as an add-on therapy or to replace completely or partially treatment with corticosteroids for chronic, prophylactic, anti-inflammatory treatment of asthma to provide a mean steady state plasma level of 1 to less than 5 mg/L. The plasma levels are achieved by preparing theophylline administrated by the oral route in a dosage form for dosing at 50 to 600 mg/day.

Barnes (Am J Respir Crit Care Med, 2003, 167:813-818), discusses the use of theophylline and steroids in combination for COPD and suggests that the combination may have a synergistic effect in reducing inflammation. However, no dosing regime is provided nor is the use of administrating theophylline by the inhaled route disclosed.

For clarity Table 1 presents a summary of the prior art in regard to oral doses of methylxanthines administrated and corresponding theophylline plasma levels detected in patients.

For clarity Table 2 presents a summary of the limited data in the prior art in regard to inhaled doses of methylxanthines administrated and corresponding theophylline plasma levels detected in asthma patients.

TABLE 1

| Publication | Study duration | Drug | Daily dose | Average theophylline plasma level |
|---|---|---|---|---|
| Alexander et al. (1980) J Am Med Assoc. 244: 2286-90 | 4 weeks | Theophylline | 400 mg | 15.1 mg/L |
| Iversen et al. (1992) Eur Respir J. 5 Suppl (15): 137. | 4 weeks | Theophylline | 600 mg | 7.1 mg/L |
| Ito et al. (2002). Proc. Natl. Acad. Sci. USA 99(13): 8921-8926 | 4 weeks | Euphylong (Theophylline) | 500 mg | 4.3 mg/L |
| Culpitt et al. (2002) Am. J. Respir. Crit Care Med. 165(10): 1371-1376 | 4 weeks | Theophylline | 300-600 mg | 9.5 mg/L |
| Kobayashi et al (2004). Respirology 9: 249-254 | 4 weeks | Theodur (Theophylline) | 400 mg | 7.9 mg/L |
| Evans et al., (2004) NEJM 337: 1412 | 12 weeks | Euphylong (Theophylline) | 500-750 mg | 8.7 mg/L |
| U.S. Pat. No. 6,025,360 (1995) | 4 weeks | Phyllocontin or Uniphylline (Theophylline) | 562-573 mg | Average not quoted but 20/25 patients had levels ≧5 mg/L |

TABLE 2

| Publication | Study duration | Drug | Dose | Net peak theophylline plasma level |
|---|---|---|---|---|
| Bohadana et al. (1980) Bull. Eur. Physiopathol. Respir. 16(1): 13-24. | Single inhaled exposure | Aminophylline (Theophylline) | 187.5 mg | 0.91 mg/L |

Thus, there is a medical need for a therapeutic regime for COPD which provides effective anti-inflammatory activity and avoids side-effects associated with existing therapies. The combination of inhaled theophylline with an inhaled steroid in the manufacture of a medicament is disclosed in our copending international patent application PCT/GB05/003039 but has not been described in the published literature. Such a medicament provides a combination therapy for COPD and other chronic respiratory diseases that may improve the pulmonary anti-inflammatory activity of the inhaled steroid. This inhaled combination produces minimal methylxanthine systemic exposure (plasma levels <1 mg/L) and therefore results in an attractive side effect profile compared with chronic oral administration.

BRIEF DESCRIPTION OF THE INVENTION

The present inventors have determined that steroids administered together with methylxanthine compounds by the inhaled route at doses which alone are not effective in treating inflammation induced by tobacco smoke (TS) in an animal model of COPD, have a synergistic effect and are able to markedly reduce inflammation in said models, for example by 44% or more in the tests set forth below. TS exposure is widely accepted to be the principal cause of COPD in human beings.

In a first aspect, therefore, there is provided the use of a methylxanthine compound and a steroid in the manufacture of a composition for the treatment of a chronic respiratory disease selected from the group consisting of chronic obstructive pulmonary disease (COPD), cystic fibrosis, steroid resistant asthma, severe asthma and paediatric asthma in a human subject, wherein the composition is administered by the inhaled route for pulmonary delivery, and the methylxanthine compound is administered at a dose between 0.1 and 25 mg/day.

Advantageously, the inhaled steroid is administered at a dose which, in isolation, is not effective in reducing the inflammation associated with the said respiratory disease. The inhaled steroid may also be administered at a dose which, in isolation, has minimal efficacy with respect to improvements in lung function and inflammation in treating said respiratory disease.

There is also provided the use of the inhaled combination wherein the inhaled steroid is administered at a lower dose than that, in isolation, has significant efficacy with respect to improvements in lung function and inflammation in treating said respiratory disease (steroid sparing).

Improving this minimal pulmonary anti-inflammatory activity of inhaled steroids (such as budesonide, fluticasone or ciclesonide) using an inhaled methylxanthine (such as theophylline) in combination provides a great benefit to patients suffering from chronic respiratory diseases such as COPD by resulting in improved health status, improved pulmonary function, improvement in measures of dyspnea and further reduced exacerbation frequency.

The invention recognises a synergistic activity between a methylxanthine compound and steroid drugs which results in an extremely high pulmonary anti-inflammatory activity. This synergy can be achieved using doses of the drugs which were ineffective when administered alone. The effect is not additive, but synergistic, in that two drugs having little or no effect can be administered simultaneously to obtain highly significant inhibition of the inflammatory response.

A methylxanthine compound, as used herein, refers to theophylline and pharmacologically equivalent compounds and salts, including aminophylline and oxtriphylline. Such compounds are methylxanthines, which include caffeine, acepifylline, bamifylline, bufylline, cafaminol, cafedrine, diprophylline, dihydroxypropyltheophylline, doxofylline, enprofylline, etamiphylline, etofylline, proxyphylline, suxamidofylline, Theobromine, Furaphylline, 7-propyl-theophylline-dopamine, Pentoxifylline, Reproterol, denbufylline, IBMX, Arofylline, Cipamfylline, HWA 448, SDZ MKS 492, BB-1502 and the like.

Steroid drugs include glucocorticoids, corticosteroids and mineralocorticoids, such as dexamethasone and budesonide, beclomethasone, beclomethasone dipropionate, flunisolide, fluticasone, Ciclesonide, mometasone, hydrocortisone, prednisone, prednisolone, methyl prednisolone, naflocort deflazacort, halopredone acetate, fluocinolone acetonide, fluocinonide, clocortolone, tipredane, prednicarbate, alclometasone dipropionate, halometasone, rimexolone, deprodone propionate, triamcinolone, betamethasone, fludrocoritisone, desoxycorticosterone, rofleponide, etiprednol dicloacetate and the like. Steroid drugs can additionally include steroids in clinical or pre-clinical development for respiratory diseases such as GW-685698, GW-799943, NCX-1010, NCX-1020, NO-dexamethasone, PL-2146, NS-126 (formerly ST-126) and compounds referred to in international patent applications WO0212265, WO0212266, WO02100879, WO03062259, WO03048181 and WO03042229. Steroid drugs can also additionally include next generation molecules in development with reduced side effect profiles such as selective glucocorticoid receptor agonists (SEGRAs), including ZK-216348 and compounds referred to in international patent applications WO-00032585, WO-000210143, WO-2005034939, WO-2005003098, WO-2005035518 and WO-2005035502.

Preferably, the methylxanthine is theophylline.

Preferably, the steroid is budesonide, fluticasone or ciclesonide.

In accordance with the invention, the steroid may be administered at a standard dose, or a dose which would have a minimal effect if administered independently of the methylxanthine compound to an individual.

Advantageously, the steroid is ineffective in reducing inflammation in said respiratory disease at the dose used. Certain respiratory diseases, including COPD, are resistant to steroid treatment and steroid drugs are minimally effective in reducing pulmonary inflammation. Together with a methylxanthine compound such as theophylline, however, a pulmonary anti-inflammatory effect is observed.

Administration takes place via the inhaled route, providing the convenience of patients receiving their target doses of an inhaled methylxanthine compound and inhaled steroid, with or without a long acting bronchodilator drug, from a single device. Typically the long acting bronchodilator drug would be either a long-acting β-agonist, such as salmeterol or formoterol, or a long acting anti-muscarinic, such as tiotropium. Administration of the steroid may also be by the oral route with the methylxanthine compound being given by inhalation.

The combinations of the invention can optionally comprise one or more additional active substances which are known to be useful in the treatment of respiratory disorders such as PDE4 inhibitors, PDE5 inhibitors, PDE7 inhibitors, leukotriene D4 inhibitors, leukotriene B4 inhibitors, inhibitors of egfr-kinase, p38 MAP kinase inhibitors, NF-κB pathway inhibitors such as IκK inhibitors, A2A adenosine receptor agonists, NFα signalling inhibitors (such as ligand binding agents, receptor antagonists), Interleukin-1 signalling inhibitors, CRTH2 receptor antagonists, protease inhibitors (such as neutrophil elastase inhibitors, MMP inhibitors, Cathepsin inhibitors), IL-8 signalling molecules, CXCR1 inhibitors, CXCR2 inhibitors, iNOS modulators, PPAR agonists, antioxidants (including N-acetylcysteine and superoxide dismutase mimetics) and/or NK-1 receptor antagonists.

In another aspect, the invention provides a pharmaceutical composition comprising a methylxanthine compound and a steroid for use in the treatment of a chronic respiratory disease selected from the group consisting of chronic obstructive pulmonary disease (COPD), cystic fibrosis, steroid resistant asthma, severe asthma and paediatric asthma, wherein the composition is adapted for administration by the inhaled route for pulmonary delivery and wherein the methylxanthine compound is administered at a dose of 0.1 to 25 mg/day.

Moreover, the invention provides a methylxanthine compound and a steroid for simultaneous, simultaneous separate or sequential use in the treatment of a chronic respiratory disease selected from the group consisting of chronic obstructive pulmonary disease (COPD), cystic fibrosis, steroid resistant asthma, severe asthma and paediatric asthma, wherein the composition is adapted for administration by the inhaled route for pulmonary delivery and wherein the methylxanthine compound is administered at a dose of 0.1 to 25 mg/day.

Preferably, the methylxanthine compound is provided in an amount from 0.1 and 25 mg, or from 0.05 to 13 mg, or from 0.033 to 9 mg per unit dose of the composition, said unit doses corresponding respectively to those for once per day, twice per day, or three times per day treatment. Preferably, the daily dose is between 1 and 24 mg, 23 mg, 22 mg, 21 mg or 20 mg. For example, the daily dose may be 5, 10, 15, 16, 17, 18 or 19 mg. Unit dosages may be calculated for once, twice or three times daily application.

Preferably, the methylxanthine compound is theophylline. Advantageously, the theophylline is administered at a dosage as set forth above.

Methylxanthines other than theophylline may be administered in the above dosages, or at dosages which may be adapted from the above by persons skilled in the art.

The steroid may be provided, in general, at a dosage of from about 40 mcg to 1600 mcg, either in a single daily does or in multiple unit doses which together add up to the stated dose. For example, the steroid may be provided in a daily dose of 50, 100, 150, 200, 250, 300, 350, 400, 450, 500, 550, 600, 750, 800, 900 or 1000 mcg.

Advantageously, the steroid is budesonide and is provided in an amount from 200 mcg to 1600 mcg, or from 100 mcg to 800 mcg mg, or from 65 mcg to 525 mcg per unit dose of the composition, said unit doses corresponding respectively to those for once per day, twice per day, or three times per day treatment. Preferably, the daily dose is between 200 mcg and 1600, 1500, 1400, 1300, 1200, 1100 or 1000 mcg; for example, the daily dose is 250, 300, 350, 400, 450, 500, 550, 600, 650, 700, 750, 800, 850 or 900 mcg. Unit dosages may be calculated for once, twice or three times daily application.

In a further embodiment the steroid is fluticasone and is provided in an amount from 44 mcg and 1000 mcg, or from 22 mcg to 500 mcg, or from 15 mcg to 335 mcg per unit dose of the composition, said unit doses corresponding respectively to those for once per day, twice per day, or three times per day treatment. Preferably, the daily dose is between 44 mcg and 900, 880, 800, 700, 660, 600 or 500 mcg; for example, the dose can be 50, 60, 88, 100, 110, 125, 150, 200, 220, 250, 300, 350, 375, 400, 440 or 450 mcg. Unit dosages may be calculated for once, twice or three times daily application.

Moreover, steroid can be Ciclesonide and be provided in an amount from 40 mcg and 500 mcg, or from 20 mcg, to 250 mg, or from 17 mcg to 170 mcg per unit dose of the composition, said unit doses corresponding respectively to those for once per day, twice per day, or three times per day treatment. The daily dose is preferably between 40 mcg and 480, 450, 400, 350, 320 or 300 mcg; for example, the dose is 80, 100, 120, 150, 160, 200 or 250 mcg. Unit dosages may be calculated for once, twice or three times daily application.

Such unit dosages may be packaged to provide a kit for the treatment of said respiratory disease, comprising a methylxanthine compound and a steroid in unit dosage form, wherein the composition is administered by the inhaled route for pulmonary delivery. For example, a kit according to the invention may comprise the methylxanthine compound and the steroid in admixture, in the correct ratio, for concurrent administration. Alternatively, the compounds may be provided as separate compositions for simultaneous separate or sequential administration.

In a particularly preferred embodiment, the methylxanthine compound and the steroid are provided in the form of an inhaler, for administration via the inhaled route. The inhaler may be a single bottle inhaler, with the compounds provided in admixture, or a twin-bottle inhaler wherein the compounds are provided separately but administered together.

Such a kit may comprise, for example, instructions for use which direct the user to administer the medicaments substantially simultaneously, such that they are present in the patient's body, particularly the lungs, at the same time.

In the kits or unit dosages according to the invention, the steroid is preferably present at a dose which is insufficient to be effective in the treatment of said respiratory disease if administered independently.

Importantly, plasma levels achieved with the doses of a methylxanthine compound such as theophylline used (total daily administered dose 0.1-25 mg) fall below those currently considered necessary for clinical efficacy (10-20 mg/l) (Cazzola et al, Pulmonary Pharmacology & Therapeutics, 2004, 17, 141-145) and those below used to demonstrate anti-inflammatory activity (5 mg/L) (Culpitt et al. Am. J. Respir. Crit Care Med, 2002, 165(10): 1371-1376, Kobayashi at al, Respirology, 2004, 9:249-254). The nominal dose quoted as being delivered may exceed this figure, depending upon the characteristics of the device and the formulation in use; however, the invention provides that an effective dose resulting in plasma levels between 1 pg/L and 1 mg/L of methylxanthine determined 1 hour post administration is effective in treating respiratory conditions when administered by the inhaled route for pulmonary delivery in combination with a steroid drug.

Preferably, the plasma level of methylxanthine compound achieved as described above is between 1 mcg/L and 1 mg/L, advantageously 100 mcg/L-1 mg/L, 25 mcg/L-1 mg/L, 500 mcg/L-1 mg/L or 750 mcg/L-1 mg/L. Advantageously, it is 950 mcg/L or less, 900 mcg/L or less, 850 mcg/L or less, or 800 mcg/L or less.

In the foregoing aspects of the invention, the dosage of steroid which does not exert any apparent pharmacological effect in the animal model of COPD is advantageously below 0.5 mg/kg, preferably between 0.1 and 0.4 mg/kg, most preferably between 0.1 and 0.3 mg/kg. Advantageously, the dose of steroid is 0.1 mg/kg or less.

There is moreover provided a method for the treatment of a chronic respiratory disease selected from the group consisting of chronic obstructive pulmonary disease (COPD), cystic fibrosis, steroid resistant asthma, severe asthma and paediatric asthma, comprising administering to a human patient in need thereof a composition according to the foregoing aspects of the invention.

The effectiveness of the treatment may be assayed, in accordance with the invention, by any technique capable of assessing inflammation. In a preferred embodiment, the treatment of the respiratory disease is assessed by counting cells recovered by bronchoalveolar lavage (BAL). Inflammation can also be assessed in sputum or in bronchial epithelial biopsies (Rutgers et al. Eur Respir J. 2000, 15(1):109-15). Non-invasive assessment of pulmonary inflammation can also be assessed using positron emission tomography and $^{18}$F-fluorodeoxyglucose uptake (Jones et al. Eur Respir J, 2003, 21: 567-573).

Advantageously, the pulmonary cells are selected from the group consisting of macrophages, neutrophils and lymphocytes.

The invention is capable of substantially reducing inflammation in respiratory diseases. Advantageously the cell count is reduced by 40% or more upon administration of a methylxanthine compound and a steroid, preferably 44%, 50%, 60% or more.

At the same time, the individual doses of a methylxanthine compound and the steroid can advantageously reduce cell numbers by a total, when added together, of 31% or less, preferably 30% or less, and ideally by 20% or less. Where the synergistic reduction of cell count on administration of a methylxanthine compound and a steroid is 40% or more, preferably 44% and advantageously 50% or more, the additive effect of the individual agents is preferably 31% or less, advantageously 20% or less.

DETAILED DESCRIPTION OF THE INVENTION

The present invention employs standard techniques of pharmacology and biochemistry, as described in more detail below. In the context of the invention, certain terms have specific meanings, as follows.

The invention describes the administration of theophylline and steroid drugs in combination, and contrasts the combined administration with individual administration of said drugs in isolation. "In isolation" accordingly refers to the administration of theophylline without a steroid, or vice versa, irrespective of whether the steroid is administered before, concomitantly with or after the theophylline. The intention is to differentiate between the theophylline and the steroid being administered such that they can exert their pharmacological activities in the target organism contemporaneously or separately.

"Combined use" or "combination" within the meaning of the present invention is to be understood as meaning that the individual components can be administered simultaneously (in the form of a combination medicament), separately but substantially simultaneously (for example in separate doses) or sequentially (directly in succession or after a suitable time interval, provided that both agents are active in the subject at the same time).

"Effective", referring to treatment of inflammatory conditions and/or respiratory disease, refers to obtaining a response in an assay which measures inflammation in respiratory disease. The preferred assay is bronchoalveolar lavage (BAL) followed by cell counting, wherein the presence of cells indicates inflammation of the lung. In human patients, BAL, induced sputum and bronchial biopsy are preferred methods of assessing inflammation. Inflammation may be induced by any desired means, such as tobacco smoke inhalation, administration of irritants such as LPS, and the like. Tobacco smoke inhalation is preferred since, as shown previously in UK patent application 0417481.9, the use of LPS does not faithfully reproduce an inflammatory response that is steroid resistant as is seen in COPD. In the context of the BAL/cell counting assay, "effective" preferably encompasses a reduction in cell numbers by 30%, 35%, 40%, 45%, 50%, 60%, 65%, 70% or more compared to a control in which the agent is not administered.

"Not effective" means, in the same assay, a much lower level of response. Preferably, in the BAL/cell counting assay, "not effective" means that the reduction in cell numbers is 30% or below, advantageously 28%, 27%, 26%, 25%, 24%, 23% 22% or 21% or below, and preferably 20% or below. In some instances, "not effective" can encompass an increase in inflammation, seen for example as an increase in cell numbers.

"Synergistic" means that the effectiveness of two agents is more than would be expected by summing their respective individual effectiveness in a given assay. For example, if theophylline and a steroid reduce cell numbers in the BAL assay by 10% and 20% respectively when administered in isolation, a synergistic response would be seen if the reduction in cell numbers were above 30%, preferably above 35%, 40%, 50% or more, in a combined administration of the same agents at the same dose.

"Administered" refers to the administration of the entire dose of the agent, such as in a bolus dose, to the intended subject. In the context of the present invention, dosage is preferably expressed in terms of plasma levels achieved (<5 mg/L; 6-9 mg/L; 10-20 mg/L) with plasma levels preferably less than 5 mg/L, and most preferably less than 1 mg/L.

A "dose" is an amount of agent administered as described above.

"Unit dosage" form is a preparation of a pharmaceutical composition in one or more packaged amounts, each of which contains a single dosage in accordance with the invention.

Methylxanthines and Steroids

Theophylline and Aminophylline

Theophylline has the structure shown below:

(I)

and is available commercially under a variety of brand names, including Accurbron, Aerobin, Aerolate, Afonilum, Aquaphyllin, Armophylline, Asmalix, Austyn, Bilordyl, Bronchoretard, Bronkodyl, Cetraphylline, Constant T, Duraphyllin, Diffumal, Elixomin, Elixophyllin, Etheophyl, Euphyllin, Euphylong, LaBID, Lanophyllin, Lasma, Nuelin, Physpan, Pro-Vent, PulmiDur, Pulmo-Timelets, Quibron, Respid, Slo-Bid, Slo-Phyllin, Solosin, Sustaire, Talotren, Teosona, Theobid, Theoclear, Theochron, Theo-Dur, Theolair, Theon, Theophyl, Theograd, Theo-Sav, Theospan, Theostat, Theovent, T-Phyl, Unifyl, Uniphyl, Uniphyllin, and Xanthium. The chemical name of Theophylline is 3,7-dihydro-1,3-dimethyl-1H-purine-2,6-dione or 1,3-Dimethylxanthine and its general chemical formula is $C_7H_8N_4O_2$.

Aminophylline

A theophylline derivative, this is synonymous with theophylline ethylenediamine. Aminophylline is a derivative of theophylline; both are methylxanthines and are derived from Xanthines. The drug aminophylline differs somewhat in its structure from theophylline in that it contains ethylenediamine, as well as more molecules of water. Aminophylline tends to be less potent and shorter acting than theophylline. Its structure is shown below:

Since a significant portion of the inhaled dose may be swallowed, it is important to note that theophylline is well absorbed from the gastrointestinal tract with up to 90-100 percent bioavailability. Peak levels are achieved within 1-2 hours following ingestion, but this is slowed by the presence of food. Theophylline is approximately 60 percent plasma protein bound and has a mean volume of distribution of 0.5 l/kg. Plasma protein binding is reduced in infants and in patients with liver cirrhosis. The mean plasma half-life of theophylline is about 8 hours in adults although there is large intra- and inter-individual variation, and also varies greatly with age being approximately 30 hours in premature neonates, 12 hours within the first 6 months, 5 hours up to the first year of life and approximately 3.5 hours up to the age of 20 gradually increasing again thereafter. Theophylline is mainly metabolised in the liver by demethylation or oxidation using the cytochrome P450 system. Only small amounts are excreted by the kidney unchanged, and dosage adjustments in renal failure are unnecessary. However, caution needs to be exercised when using other drugs that are also metabolised by the cytochrome system when dosage adjustments need to be made in conjunction with the measurement of plasma levels. Many drugs may interfere with the metabolism of theophylline. Special care should be taken with certain antibiotics as patients with acute infective exacerbations of their airways obstruction may be inadvertently put on them without consideration of the effects on theophylline metabolism. These include the macrolide (e.g. erythromycin) and quinolone (e.g. ciprofloxacin) families of antibiotics which both reduce theophylline clearance to varying degrees. Other drugs that reduce theophylline clearance include cimetidine, allopurinol and propanolol (although this would be a rather unusual therapeutic combination). Drugs that increase theophylline metabolism include rifampicin, phenobarbitone and particularly phenyloin and carbamazepine but not the oral contraceptive pill. The rate of metabolism of theophylline is increased substantially in cigarette smokers (the half life can be halved), although may not be significant in those who smoke less than 10/day. Smoking marijuana has a similar effect as can eating a high protein diet. Hepatic dysfunction, heart failure and cor pulmonale all reduce the elimination of theophylline, and low albumin states reduce the amount of protein bound drug in the blood, so results of plasma levels need to be interpreted with caution. Therefore, as the clinical state of the patient with heart failure or respiratory failure with cor pulmonale improves, the clearance of theophylline alters, and dosage adjustments may be necessary.

Administering the methylxanthine by the inhaled route for pulmonary delivery is not only desirable to maximise the locally mediated pulmonary anti-inflammatory synergy with the inhaled steroid, but also to administer the methylxanthine at lower doses (<25 mg) resulting in minimal systemic exposure (<1 mg/L). Very low methylxanthine plasma levels may significantly reduce the incidence of the systemic side effects of standard oral methylxanthine therapy described above.

Methylxanthines

Methylxanthine compounds, which include theophylline and aminophylline, have the general formula Wherein
X represents hydrogen, an aliphatic hydrocarbon radical or —CO—$NR_3R_4$;
$R_1$, $R_2$ and $R_3$ represent aliphatic hydrocarbon radicals;
$R_4$ represents hydrogen or an aliphatic hydrocarbon radical and $R_3$ and $R_4$ together with the nitrogen atom may also represent an alkylene imino radical with 5 to 6 ring members or the morpholino radical; and
$R_5$ represents hydrogen or an aliphatic hydrocarbon radical.

All such compounds are within the scope of the present invention; however, theophylline itself is especially preferred.

Steroids

Steroid drugs in general are suitable for use in the present invention. Particular steroids are set forth below.
Common inhaled steroids include:
Pulmicort® (budesonide)
Flovent® (fluticasone)
Asmanex® (mometasone)
Alvesco® (cilcesonide)
Aerobid® (flunisolide)
Azmacort® (triamcinolone)
Qvar® (beclomethasone HFA)
Steroids may also be administered in the form of combinations with long acting bronchodilators with a range of mechanisms including beta 2 adrenergic agonists (such as formoterol or salmeterol) and/or muscarinic antagonists such as ipratropium and tiotropium. The bronchodilator included in the steroid combination can have beta 2 adrenergic agonist and muscarinic antagonist activity in the same molecule.

Advair® (Flovent® and Serevent®) Note: Serevent® is the long acting beta-agonist salmeterol.

Symbicort® (Pulmicort® and Oxis®) Note: Oxis is the long acting beta-agonist formoterol.

Other steroid/B2 agonist combinations are in clinical development such as Ciclesonide and formoterol, and fluticasone and formoterol (Flutiform). These products may also benefit from combination therapy with inhaled theophylline.

Common steroid pills and syrups include:

Deltasone® (prednisone)

Medrol® (methylprednisolone)

Orapred®, Prelone®, Pediapred® (prednisolone)

Budesonide

Chemical name: $C_{25}H_{34}O_6$: 430.54 (+) [(RS)-16a,17a-Butylidenedioxy-11b,21-dihydroxy-1,4-pregnadiene-3,20-dione]

CAS Registry Number: 51333-22-3

Budesonide was originally synthesised from 16a-hydroxyprednisolone. The unique structure of the molecule is the key to its combination of high topical anti-inflammatory potency with relatively low potential for systemic side-effects. In addition, budesonide is both sufficiently water soluble for easy dissolution in mucosal fluids and lipid soluble for rapid uptake by mucosal membranes.

Because the acetal group is asymmetrical, budesonide exists as a 1:1 mixture of two epimers, known as 22R and 22S.

Fluticasone

BRAND_NAMES: Cutivate, Flixonase, Flixotide, Flonase, Flovent, Flunase

CHEMICAL_NAME:
(6(,11(,16(,17( )-6,9-difluoro-1-hydroxy-16-methyl-3-oxo-17-(1-oxopropoxy)androsta-1,4-diene-17-carbothioic acid S-(fluoromethyl)ester

CHEMICAL_FORMULA: $C_{25}H_{31}F_3O_5S$

CAS_NUMBER: 80474-14-2

Cidesonide

BRAND_NAMES: Alvesco

CHEMICAL_NAME:
(R)-11beta,16alpha,17,21-Tetrahydroxypregna-1,4-diene-3,20-dione, cyclic 16,17-acetal with cyclohexanecarboxaldehyde, 2'-isobutyrate

CHEMICAL_FORMULA: $C_{32}-H_{44}-O_7$

CAS_NUMBER: 141845-82-1

Beclomethasone

CHEMICAL_NAME
(11(16( )-9-chloro-11,17,21-trihydroxy-16-methylpregna-1,4-diene-3,20-dione CHEMICAL_FORMULA
$C_{22}H_{29}ClO_5$

CAS_NUMBER
4419-39-0

BRAND NAMES (VARIANT)
Aerobec (beclomethasone dipropionate), Aldecin (beclomethasone dipropionate), Anceron (beclomethasone dipropionate), Andion (beclomethasone dipropionate), Beclacin (beclomethasone dipropionate), Becloforte (beclomethasone dipropionate), Beclomet (beclomethasone dipropionate), Beclorhinol (beclomethasone dipropionate), Becloval (beclomethasone dipropionate), Beclovent (beclomethasone dipropionate), Becodisks (beclomethasone dipropionate), Beconase (beclomethasone dipropionate), Beconasol (beclomethasone dipropionate), Becotide (beclomethasone dipropionate), Clenil-A (beclomethasone dipropionate), Entyderma (beclomethasone dipropionate), Inalone (beclomethasone dipropionate), Korbutone (beclomethasone dipropionate), Propaderm (beclomethasone dipropionate), Qvar (beclomethasone dipropionate), Rino-Clenil (beclomethasone dipropionate), Sanasthmax (beclomethasone dipropionate), Sanasthmyl (beclomethasone dipropionate), Vancenase (beclomethasone dipropionate), Vanceril (beclomethasone dipropionate), Viarex (beciomethasone dipropionate), and Viarox (beclornethasone dipropionate).

Triamcinolone

BRAND_NAMES
Aristocort, Aristospan, Azmacort, Kenalog Nasacort
CHEMICAL_NAME
(11(,16( )-9-fluoro-11,21-dihydroxy-16,17-[1-methyleth-ylidenebis(oxy)]pregna-1,4-diene-3,20-dione
CHEMICAL_FORMULA
$C_{24}H_{31}FO_6$
CAS_NUMBER
76-25-5
Salmeterol/Advair
BRAND_NAMES
*1-hydroxy-2-naphthoate*1-hydroxy-2-naphthoate: Arial, Salmetedur, Serevent
CHEMICAL_NAME
(( )-4-hydroxy-('[[[6-(4-phenylbutoxy)hexyl]amino]methyl] 1,3-benzenedimethanol
CHEMICAL_FORMULA
$C_{25}H_{37}NO_4$
CAS_NUMBER
89365-50-4

Methylprednisolone

CHEMICAL_NAME
(6(,11( )-11,17,21-trihydroxy-6-methylpregna-1,4-diene-3,20-dione
CHEMICAL_FORMULA
$C_{22}H_{30}O_5$
CAS_NUMBER
83-43-2
BRAND_NAMES
Medrate, Medrol, Medrone, Metastab, Metrisone, Promacortine, Suprametil, Urbason
Prednisone BRAND_NAMES
Ancortone, Colisone, Cortancyl, Dacortin, Decortancyl, Decortin, Delcortin, Deltacortone, Deltasone, Deltison, Di-Adreson, Encorton, Meticorten, Nurison, Orasone, Paracort, Prednilonga, Pronison, Rectodelt, Sone, Ultracorten
CHEMICAL_NAME
17,21-dihydroxypregna-1,4-diene-3,11,20,trione
CHEMICAL_FORMULA
$C_{21}H_{26}O_5$
CAS_NUMBER
53-03-2
Formulation Xanthine derivatives such as theophylline and aminophylline are available in a variety of pharmaceutical preparations. Likewise, steroid drugs are widely available in a variety of formulations. Formulations used in the examples described herein are further detailed below, but any formulation may be used in the present invention which allows inhaled delivery (oral or nasal inhalation) of the drugs to the subject in the desired dosage.

Preferred compositions for use according to the invention may suitably take the form of tablets, blisters, capsules, granules, spheroids, powders or liquid preparations.

In this invention theophylline is administered in inhaled foam. Aerosol generation can be carried out, for example, by pressure-driven jet atomizers or ultrasonic atomizers, but advantageously by propellant-driven metered aerosols or propellant-free administration of micronized active compounds from, for example, inhalation capsules or other "dry powder" delivery systems. Steroid drugs may be administered by either the oral or inhaled route. Advantageously, the steroid drugs are administered by the inhaled route.

The active compounds are dosed as described depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparata are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Accuhaler®, Turbohaler®, Clickhaler®, Duohaler®, Evohaler®, Twisthaler®, Aerobec, Airmax, Skye-Haler, HandiHaler®, Respimat® Soft Mist™ Inhaler) or other inhalers for example as described in European Patent Applications EP 0 505 321, EP 407028, EP 650410, EP 691865 or EP 725725).

Respiratory diseases treated by the present invention specifically include COPD (bronchitis, obstructive bronchitis, spastic bronchitis, emphysema), cystic fibrosis, steroid resistant asthma (including smoking asthmatics) and paediatric asthma which can be treated by the combination according to the invention. The synergistic combination of the invention is particularly indicated in long-term therapy, since lower quantities of drugs are needed than in conventional monotherapies.

1. Materials

Compounds were purchased from an external supplier. Carboxymethyl-cellulose (CMC) (Na salt) (product code C-4888) was obtained from Sigma. Phosphate buffered saline (PBS) was obtained from Gibco. Sterile saline (0.95 w/v NaCl) and Euthatal (sodium pentobarbitone) were obtained from Fresenius Ltd. and the Veterinary Drug Company respectively.

The tobacco smoke was generated using 1R1 cigarettes purchased from the Institute of Tobacco Research, University of Kentucky, USA.

Mice

Female inbred A/J mice (body weights on initial day of use: ~20 g) were obtained from Harlan, full barrier bred and certified free from specified micro-organisms on receipt. The mice were housed, up to 5 per cage, in individually ventilated, polycarbonate solid bottomed cages (IVC) with grade 8 aspen chip bedding. Environment (airflow, temperature and humidity) within the cages was controlled by the IVC system (Techniplast). Food (RM 1, Special Diet Services) and water were provided ad libitum, Individual animals were identified by unique coloured "pentel" markings on their tails, weighed and randomly assigned to treatment groups.

2. Formulation

Frequency of formulation: Compounds were formulated fresh every day prior to each intra-nasal (i.n.) or oral dosing.

3.0 Methods

Previous studies have established that the total numbers of cells recovered in the BAL are significantly elevated 24 h following the final TS exposure of 11 consecutive daily TS exposures, this time point was used in the study reported here.

Protocols for the exposure of mice to TS, obtaining bronchoalveolar lavage (BAL), preparation of cytospin slides for differential cell counts are as outlined below.

Exposure of Animals to Ts Daily for 11 Consecutive Days

In this exposure protocol, mice were exposed in groups of 5 in individual clear polycarbonate chambers (27 cm×16 cm×12 cm). The TS from the cigarettes was allowed to enter the exposure chambers at a flow rate of 100 ml/min. In order to minimise any potential problems caused by repeated exposure to a high level of TS (6 cigarettes), the exposure of the mice to TS was increased gradually over the exposure period to a maximum of 6 cigarettes. The exposure schedule used in this study was as follows:

Day 1: 2 cigarettes (approximately 16 min exposure)
Day 2: 3 cigarettes (approximately 24 min exposure)
Day 3: 4 cigarettes (approximately 32 min exposure)
Day 4: 5 cigarettes (approximately 40 min exposure)
Day 5 to 11:6 cigarettes (approximately 48 min exposure)

A further group of mice were exposed to air on a daily basis for equivalent lengths of time as controls (no TS exposure).

Bronchoalveolar Lavage and Cytospin Analysis

Bronchoalveolar lavage was performed as follows:

The trachea was cannulated using a Portex nylon intravenous cannula (pink luer fitting) shortened to approximately 8 mm. Phosphate buffered saline (PBS) containing heparin (10 units/ml) was used as the lavage fluid. A volume of 0.4 ml was gently instilled and withdrawn 3 times using a 1 ml syringe and then placed in an Eppendorf tube and kept on ice prior to subsequent determinations.

Cell counts:

Lavage fluid was separated from cells by centrifugation and the supernatant decanted and frozen for subsequent analysis. The cell pellet was re-suspended in a known volume of PBS and total cell numbers calculated by counting a stained (Turks stain) aliquot under a microscope using a haemocytometer.

Differential cell counts were performed as follows:

The residual cell pellet was diluted to approximately $10^5$ cells per ml. A volume of 500 µl was placed in the funnel of a cytospin slide and centrifuged for 8 min at 800 rpm. The slide was air dried and stained using 'Kwik-Diff' solutions (Shandon) as per the proprietary instructions. When dried and cover-slipped, differential cells were counted using light microscopy. Up to 400 cells were counted by unbiased operator using light microscopy. Cells were differentiated using standard morphometric techniques.

Pharmacokinetic Evaluation of Plasma Levels of Theophylline after Oral or i.n Dosing in Ts Exposed A/J Mice The mice were terminally anaesthetised and blood collected by cardiac puncture into syringes containing 20U lithium Heparin in 5u1. The collected blood was mixed and decanted into eppendorf tubes before centrifugation in a microfuge. Plasma was collected and stored at −80° C. prior to analysis by an HPLC/MS/MS method. The equipment used in the measurement of plasma levels were a Micromann Quatro Micro Mass Spectrometer (Micromass UK Limited) and a Waters 2795 Alliance HT liquid chromatograph (Waters USA).

Six reference standard concentrations were prepared by spiking mouse plasma with stock concentrations of theophylline dissolved in methanol. Samples were prepared for analysis by adding 200 µl of acetonitrile (containing 0.25 mg/l dextrorphan as an internal standard) to 50 µl of each thawed sample and standard and mixed vigorously. Each sample and standard was then centrifuged at 10000 g for 2 minutes and the supernatant removed for LC-MS/MS analysis.

Analysis of theophylline and dextrorphan was carried out using reverse phase HPLC with tandem mass spectrometric detection (LC-MS/MS). Positive ions for parent compound and a specific fragment product were monitored in a Multiple Reaction Monitoring mode using a Micromass Quatro Micro Mass Spectrometer with Micromass MassLynx software version 4.0. A 25 µl aliquot of each sample and standard was injected onto the liquid chromatography system. Lowest order of quantification (LOQ) was determined as 0.016 mg/L with the detection limit being 0.003 mg/L.

3.1 Treatment Regimes

For the oral dose study, mice received vehicle (1% carboxymethyl cellulose), theophylline (3 mg/kg), dexamethasone (0.3 mg/kg), a theophylline/dexamethasone combination (at 3 and 0.3 mg/kg respectively) or a theophylline/dexamethasone combination (at 1 and 0.3 mg/kg respectively) at 1 hour prior to and 6 hours post tobacco smoke exposure (−1 h and +6 h) on each of the 11 days. In addition, animals receiving steroid or the steroid combination were dosed with steroid 20 h prior to the first TS exposure. Mice were additionally dosed 1 hour prior to sacrifice on the $12^{th}$ and final day (23 hrs post the last exposure). The control group of mice received vehicle on days 1 to 12 and were exposed to air daily for a maximum of 50 minutes per day. BAL and plasma collection was performed on day 12, 24 h following the eleventh and final TS exposure.

For the intra-nasal dose study, mice received vehicle (PBS), theophylline (0.5 mg/kg), dexamethasone (0.1 mg/kg), a theophylline/dexamethasone combination (at 0.5 and 0.1 mg/kg respectively) a theophylline/dexamethasone combination (at 0.25 and 0.1 mg/kg respectively) or a theophylline/dexamethasone combination (at 0.1 and 0.1 mg/kg respectively) at 1 hour prior to tobacco smoke exposure on each of the 11 days. In addition, animals receiving steroid or the steroid combination were dosed with steroid 20 h prior to the first TS exposure. Mice were additionally dosed 1 hour prior to sacrifice on the $12^{th}$ and final day (23 hrs post the last exposure). The control group of mice received vehicle on days 1 to 12 and were exposed to air daily for a maximum of 50 minutes per day. BAL and plasma collection was performed on day 12, 24 h following the eleventh and final TS exposure.

3.2 Data Measurement and Statistical Analysis

All results are presented as individual data points for each animal and the mean value was calculated for each group.

Since tests for normality were positive the data was subjected to a one way analysis of variance test (ANOVA), followed by a Bonferroni correction for multiple comparisons in order to test for significance between treatment groups. A "p" value of <0.05 was considered to be statistically significant. Percentage inhibitions were automatically calculated within the Excel spreadsheets for the cell data using the formula below:

$$\% \text{ Inhibition} = 1 - \left(\frac{\text{Treatment group result} - \text{sham group result}}{\text{TS vehicle group result} - \text{sham group result}}\right) \times 100$$

Inhibition data for other parameters were calculated manually using the above formula.

4.0 Results 4.1 Inflammatory Response in the Bronchoalveolar Lavage Induced by Eleven Daily Consecutive Exposures to TS (24 h Post Final Exposure)

In this study exposure to TS for 11 consecutive days induced an inflammatory response 24 h following the final exposure. This consisted of significant increases in BAL of neutrophils, macrophages and lymphocytes when compared with air exposed mice (all P<0.001).

4.2 Effect of Theophylline, Dexamethasone and a Theophylline/Dexamethasone Combination on the Inflammatory Response Induced in the Bronchoalveolar Lavage by Eleven Daily Consecutive Exposures to TS (24 h Post Final Exposure)

Figure 1:
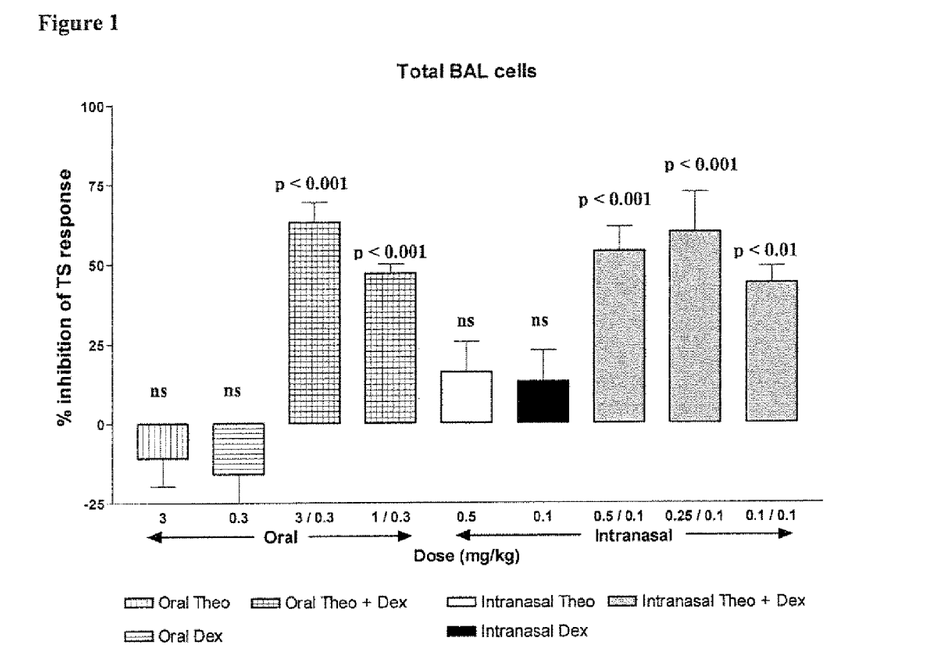
FIG. 1 Effect of Theophylline. Dexamethasone or their combination, administered orally or intra-nasally, on total cell numbers recovered in the BAL 24 hr post final exposure.
Figure 3:
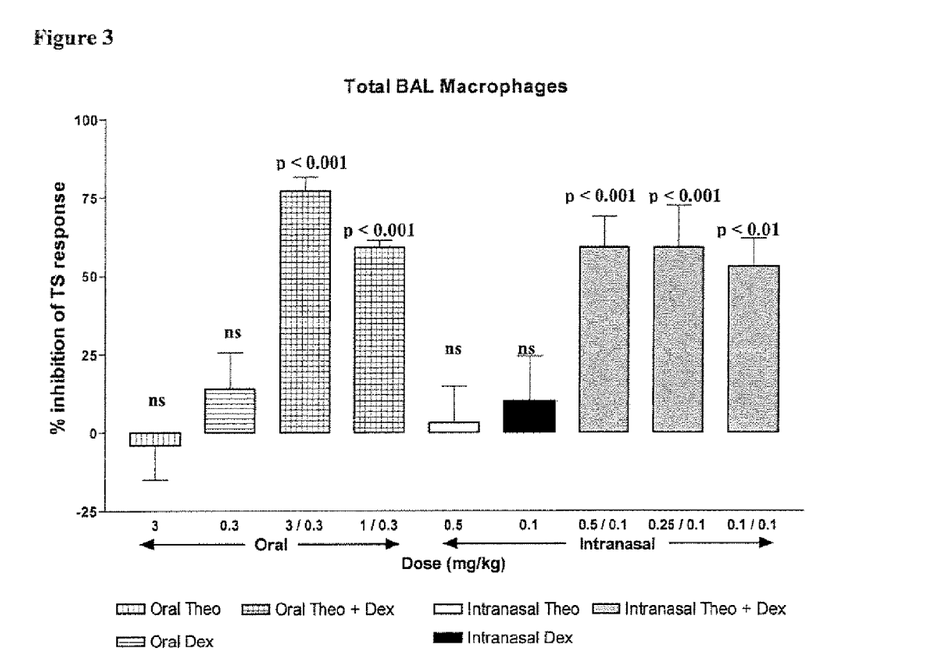
FIG. 3 Effect of Theophylline, Dexamethasone or their combination, administered orally or intra-nasally, on macrophage numbers recovered in the BAL 24 hr post final exposure.
Figure 4:
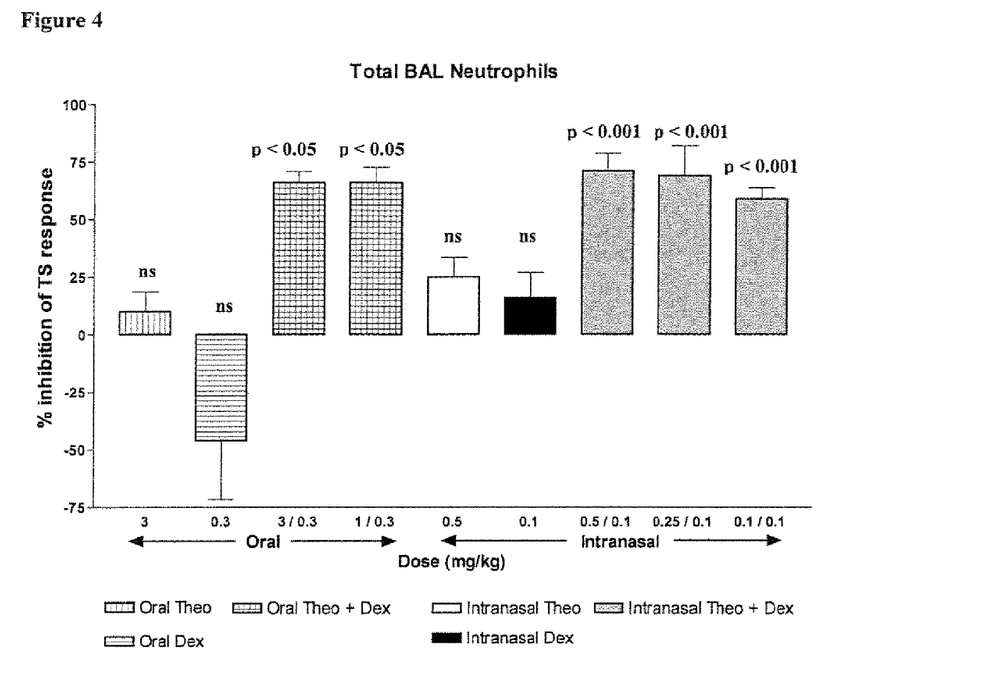
FIG. 4 Effect of Theophylline, Dexamethasone or their combination, administered orally or intra-nasally, on neutrophil numbers recovered in the BAL 24 hr post final exposure.
Figure 5:
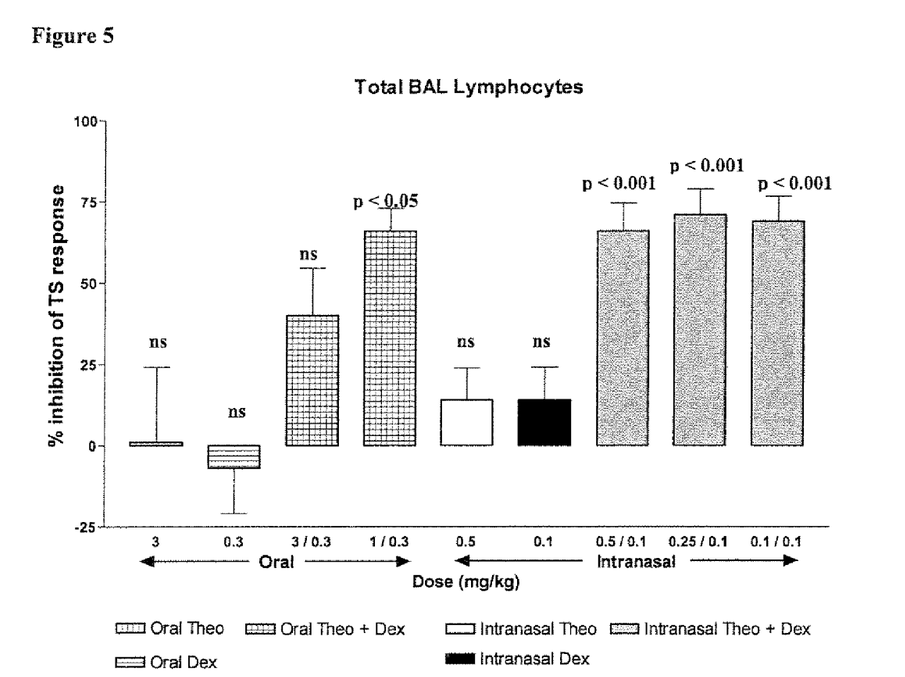
FIG. 5 Effect of Theophylline, Dexamethasone or their combination, administered orally or intra-nasally, on lymphocyte numbers recovered in the BAL 24 hr post final exposure.

Neither theophylline nor dexamethasone monotherapy when given orally or by the intra-nasal route significantly inhibited the total number of cells recovered in the BAL induced by TS exposure (FIG. 1). No statistically significant inhibitory effect was seen on any of the specific cell types (FIGS. 3-5).

In contrast, the combination of theophylline/dexamethasone at all doses examined whether given orally or by the intra-nasal route significantly inhibited the total number of cells recovered in the BAL by 44-63% (p<0.001) (FIG. 1). This effect on total cells was comprised of inhibition of macrophages, neutrophils and lymphocytes (FIG. 3-5).

A full breakdown of the inhibition of TS induced inflammatory cell infiltrate by the combination therapy is presented in Table 1.

4.3 Pharmacokinetic Analysis

Figure 2:
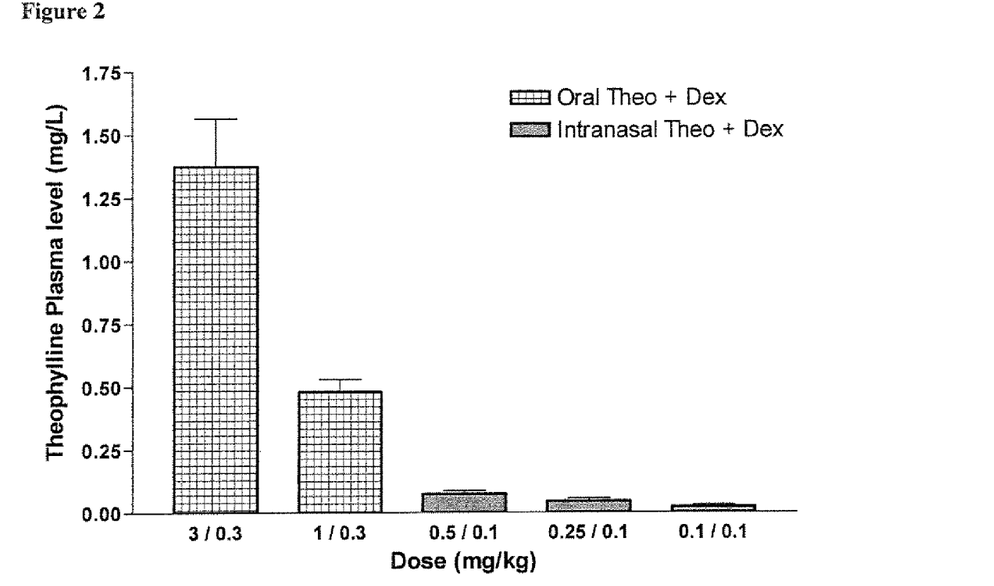
FIG. 2 Plasma levels of Theophylline at 1 hr post administration when administered in combination with Dexamethasone by either the oral or intranasal route in TS exposed mice.

Mice received a final dose of the respective theophylline/Dexamethasone combination therapy 1 hour prior to sacrifice and the plasma from these mice was examined for theophylline content. Mice dosed with the oral combination therapy had higher mean theophylline plasma content compared with those mice that received intra-nasal combination therapy (FIG. 2).

Oral combination therapy using 3 mg/kg or 1 mg/kg theophylline in combination with 0.3 mg/kg Dexamethasone resulted in mean theophylline plasma levels of 1.37±0.192 mg/L and 0.479±0.047 mg/L respectively. Intra-nasal combination therapy using 0.5 mg/kg, 0.25 mg/kg or 0.1 mg/kg theophylline in combination with 0.1 mg/kg Dexamethasone resulted in mean theophylline plasma levels of 0.074±0.013 mg/L, 0.045±0.010 mg/L and 0.022±0.009 mg/L respectively. At the doses used intra-nasal administrated theophylline resulted in very low (<0.1 mg/L) systemic theophylline exposure 1 hour post dosing.

5.0 Discussion

In this study daily treatment with theophylline or steroid monotherapy failed to have any inhibitory activity in this pulmonary inflammation model of COPD. This lack of pulmonary anti-inflammatory activity was observed whether the monotherapy was administered by the oral route or a surrogate route for inhalation (intra-nasal dosing). However, when the compounds were co-administered (by either the oral or intra-nasal route) at the same doses as given alone significant anti-inflammatory activity was demonstrated. Furthermore, lower doses of theophylline in combination with dexamethasone were also efficacious.

Moreover, the efficacy observed when the combination therapy was administered by the intra-nasal route was equivalent to the efficacy observed when the combination therapy was administered by the oral route despite low doses of both theophylline and dexamethasone being used. This suggests the efficacy is being driven by local (lung specific) anti-inflammatory activity. This [hypothesis] is further supported by examining the theophylline content of the plasma, as intra-nasal administration produced very low systemic levels (<0.1 mg/L). As an illustration, the efficacy observed with oral combination therapy (1 mg/kg theophylline/0.3 mg/kg dexamethasone) on BAL total cells (47% inhibition) was similar to that observed with intra-nasal combination therapy (0.1 mg/kg theophylline/0.1 mg/kg dexamethasone) (44% inhibition) when the steroid was given at 3 times lower dose and theophylline at 10 times lower dose. Furthermore, systemic theophylline levels were ~17 times lower in this example. Taken together, this data suggests that the combination therapy of theophylline and a steroid produces a synergistic pulmonary anti-inflammatory response that is mediated in vivo specifically within the lung.

These data demonstrate the steroid insensitivity of the mouse sub chronic TS model and furthermore reinforce the synergistic effect of combining a steroid at a therapeutic dose with an inactive dose of theophylline as a treatment paradigm for COPD. Critically, this effect is achieved when the combination therapy is administered by a surrogate for the inhaled route which permits very low doses of theophylline to be given resulting in plasma levels much lower than those normally associated with anti-inflammatory activity (5 mg/L).

per day, which for an average patient (70 kg) is equivalent to 2.9 mcg/kg-22.9 mcg/kg. In a mouse model of asthma, Budesonide at a dose of 350 mcg/kg was efficacious but doses of 35 mcg/kg or 3.5 mcg/kg were not when administered intra-nasally (Shen et al. Am. J. Respir. Crit Care Med. 2002, 166(2): 146-153).

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry, molecular

TABLE 1

Summary of the effects of theophylline, dexamethasone or their combination on TS induced BAL inflammation observed 24 hrs following 11 daily exposures

| Treatment | BAL Inflammatory markers | | | |
| --- | --- | --- | --- | --- |
| | Total cells | macrophages | neutrophils | lymphocytes |
| | % Inhibition (p value) | | | |
| Oral dosing | | | | |
| Theophylline (3 mg/kg) | −11% (ns) | −4% (ns) | −10% (ns) | 1% (ns) |
| Dexamethasone (0.3 mg/kg) | −16% (ns) | −14% (ns) | −46% (ns) | −7% (ns) |
| Theophylline (3 mg/kg + Dexamethasone (0.3 mg/kg) | 63% ($p < 0.001$) | 77% ($p < 0.001$) | 66% ($p < 0.05$) | 40% (ns) |
| Theophylline (1 mg/kg + Dexamethasone (0.3 mg/kg) | 47% ($p < 0.001$) | 59% ($p < 0.001$) | 66% ($p < 0.05$) | 66% ($p < 0.05$) |
| Intra-nasal dosing | | | | |
| Theophylline (0.5 mg/kg) | 16% (ns) | 3% (ns) | 25% (ns) | 14% (ns) |
| Dexamethasone (0.1 mg/kg) | 13% (ns) | 10% (ns) | 16% (ns) | 14% (ns) |
| Theophylline (0.5 mg/kg + Dexamethasone (0.1 mg/kg) | 54% ($p < 0.001$) | 60% ($p < 0.001$) | 64% ($p < 0.001$) | 63% ($p < 0.001$) |
| Theophylline (0.25 mg/kg + Dexamethasone (0.1 mg/kg) | 60% ($p < 0.001$) | 59% ($p < 0.001$) | 69% ($p < 0.001$) | 71% ($p < 0.001$) |
| Theophylline (0.1 mg/kg + Dexamethasone (0.1 mg/kg) | 44% ($p < 0.01$) | 53% ($p < 0.01$) | 59% ($p < 0.001$) | 69% ($p < 0.001$) | ns = not statistically different from TS/vehicle group.

The in vivo studies detailed above demonstrating the synergistic anti-inflammatory activity of the pulmonary delivered combination of theophylline and the steroid Dexamethasone using intra-nasal dosing are repeated using other steroids including Fluticasone, Budesonide or Ciclesonide. Dosages for the steroids are in the range of 1 mcg/kg/day to 1 mg/day.

It is widely accepted to those skilled in the art that doses required for efficacy of inhaled drugs administered to animals can be significantly different to those doses required for efficacy in human individuals. This is particularly the case for inhaled steroids. Efficacious doses of inhaled steroids administered to patients with respiratory diseases are typically in the range of 40 mcg to 1600 mcg (total dose regardless of body weight of the individual) depending on the steroid used and many other factors. Doses of inhaled steroids administered to animals are described in mass per unit body weight (e.g. mg/kg) rather than absolute dose. Converting the clinically used doses into mcg/kg allows comparisons between human and animal doses to be compared and demonstrates significant differences. For example, Budesonide is typically administered to patients in the range of 200 mcg-1600 mcg biology and biotechnology or related fields are intended to be within the scope of the following claims.

The invention claimed is:

1. A method for the treatment of chronic obstructive pulmonary disease (COPD), comprising administering by the inhaled route for pulmonary delivery to a human subject in need thereof a composition comprising theophylline at a dose of 0.033 to 25 mg/day and a corticosteroid in an amount effective to treat said COPD.

2. The method of claim 1, wherein the theophylline is administered in an amount of 0.05 to 12.5 mg two times per day.

3. The method of claim 1, wherein the theophylline is administered in an amount of 0.033 to 8 mg three times per day.

4. The method of claim 1, wherein the composition comprises one or more pharmaceutically acceptable additives, diluents and/or carriers.

5. The method of claim 1, wherein the theophylline is administered at a dose that achieves plasma levels between 1 pg/L and 1 mg/L.

6. The method of claim 1, wherein the inhaled steroid administered is selected from the group consisting of budesonide, fluticasone and ciclesonide.

7. The method of claim 1, wherein the inhaled corticosteroid is budesonide.

8. The method of claim 7, wherein budesonide is administered at doses between 200 mcg and 1600 mcg per day.

9. The method of claim 1, wherein the inhaled corticosteroid is fluticasone.

10. The method of claim 9, wherein fluticasone is administered at doses between 44 mcg and 1000 mcg per day.

11. The method of claim 1, wherein the inhaled corticosteroid is ciclesonide.

12. The method of claim 11, wherein ciclesonide is administered at doses between 40 mcg and 500 mcg per day.

13. The method of claim 1, wherein the corticosteroid and theophylline are co-administered.

\* \* \* \* \*